United States Patent
Sumiya et al.

(10) Patent No.: US 6,263,728 B1
(45) Date of Patent: Jul. 24, 2001

(54) METHOD OF ANALYZING FRICTIONAL ENERGY OF ROLLING TIRE

(75) Inventors: Yoshiro Sumiya; Hiroaki Sugimoto, both of Osaka (JP)

(73) Assignee: Toyo Tire & Rubber Co., Ltd., Osaka (JP)

( * ) Notice: Subject to any disclaimer, the term of this patent is extended or adjusted under 35 U.S.C. 154(b) by 0 days.

(21) Appl. No.: 09/481,655

(22) Filed: Jan. 11, 2000

(30) Foreign Application Priority Data

Aug. 10, 1999 (JP) .................................................. 11-226066

(51) Int. Cl.[7] .................................................. G01M 17/02
(52) U.S. Cl. ...................................................... 73/146; 73/8
(58) Field of Search .................................. 73/146, 9, 7, 8

(56) References Cited

U.S. PATENT DOCUMENTS

| | | | |
|---|---|---|---|
| 3,893,330 | * 7/1975 | Shute et al. | 73/146 |
| 4,187,714 | * 2/1980 | Cox et al. | 73/9 |
| 4,594,878 | * 6/1986 | Abe et al. | 73/146 |
| 4,779,447 | * 10/1988 | Rath | 73/9 |
| 5,801,304 | * 9/1998 | Cantu et al. | 73/146 |
| 5,864,056 | * 1/1999 | Bell et al. | 73/146 |
| 5,874,670 | 2/1999 | Doda et al. | |

FOREIGN PATENT DOCUMENTS 8-29296   2/1996  (JP) .

* cited by examiner

*Primary Examiner*—Max Noori
(74) *Attorney, Agent, or Firm*—Jordan and Hamburg LLP

(57) ABSTRACT

To provide a method capable of easily analyzing frictional energy of a rolling tire, in-plane pressure Pxy(L) and vertical pressure Pz(L) at one point of a tread produced by rolling the tire are measured, static frictional force R(L) is calculated and the frictional energy is calculated by determining a portion corresponding to the static frictional force R(L) equal to or larger than a primary maximum value as a slipping region LR.

2 Claims, 6 Drawing Sheets

METHOD OF ANALYZING FRICTIONAL ENERGY OF ROLLING TIRE

BACKGROUND OF THE INVENTION

1. Field of the Invention

The present invention relates to a method of analyzing frictional energy in a contact surface of rolling tire which is dissipated as wear of tread rubber.

2. Description of the Related Art

There are following technologies of predicting wear of a surface of a tread of a tire.

According to a first method, a tire is rolled in a state in which a coating is regularly coated on a surface of a tread of a tire, a degree of abrasion of the coating is recorded as a plurality of pieces of image information at required time intervals, the respective pieces of image information are divided into a number of pixels and stored, the respective pixels in correspondence with portions coated with the coating, are weighted with a magnitude inversely proportional to a time period of abrasion of the coating, further, such an abrasion information at the portions coated with the coating is converted into abrasion information in a wide region expanded to respective pixels including also portions not coated with the coating by calculating an abrasion level value in consideration of weights of their own and weights of peripheral pixels with regard to the respective pixels including the portions not coated with the coating, and the respective abrasion level values are constituted into a map to thereby predict a situation of causing irregular wear at the surface of the tread by the mapped information (U.S. Pat. No. 5874670).

According to a second method, a coating having a brightness which differs considerably from that of a surface of a land portion and deformed by following deformation of the surface of the land portion, is regularly coated on the surface of the land portion of a tire in a shape of lattice, net mesh or dots, thereafter, the tire is additionally rolled on a road surface and a situation of causing wear is predicted from a degree of abrasion of the coating (Japanese Patent Laid-Open No. 08029296 A/1996).

In both of the first and the second methods, a coating is coated on the surface of the tire and the state of wearing tire is predicted thereby and therefore, there poses a problem in which the coating must be coated in the measuring operation.

A third method is a method in which wear of a tread band of a tire is predicted and controlled based on a cut-in portion having a shallow depth formed on an outer face of a tread band at a thickness portion of a material like elastomer (U.S. Pat. No. 5801304).

According to the third method, a plurality of cut-in portions in the radius direction need to be formed at portions on an outer face of the tread band in the radius direction and there poses a problem in which the method is not preferable as the method of analyzing the surface of the tire.

According to a fourth method, a sum of frictional energy is calculated over an entire contact length to substitute for wear energy.

The method is as follows specifically.

A wear shape of a tread is predicted by measuring pressure and displacement in the forward and rearward direction and the left and right direction within the contact patch accompanied by rolling the tire by sampling at constant intervals and depending on a sum $\Sigma E$ of frictional energy at respective measuring points by a calculation using the data and an in-plane distribution thereof.

A generally known calculating method is as follows.

Frictional energy $\Sigma E$ is calculated as a sum of integrating frictional energy at respective sampling intervals provided with an inner product of displacement vectors calculated from difference values of measured displacements and in-plane pressure vectors from a front end to a rear end of contact. When the integrated value $\Sigma E$ is regarded to correspond to frictional energy dissipated in the contact patch, a wear amount of tread rubber seems to be proportional thereto.

That is, the frictional energy $\Sigma E$ is represented by the following equation.

$$\Sigma E = \int Pxy \cdot dS$$

Incidentally, integration is carried out by a sum within the contact length L.

However, according to the fourth method, there poses the following problem.

In the case of a heavy load tire (hereinafter, referred to as TB tire) satisfying a wide condition of use from a short distance (short life) to a long distance (long life) and supporting a heavy load by the same tire, there causes inconsiderable occurrence of running slippage as in a small-sized tire for low load, which does not necessarily coincide with a result of analysis.

What seems to be the cause of the in coincidence resides in that the frictional energy is integrated throughout the contact patch.

That is, the frictional energy is integrated over the entire contact length on the premise that slippage is caused over the entire contact patch. In comparing a property of a small-sized tire having low rigidity/low load which is liable to cause slippage inherently with a result of wear test integrated with intentionally slipping curved running, such an analysis method is less problematic. Further, rubber compound of a small-sized tire is softer than that of the large-sized tire and the small-sized tire is worn when excessive vertical pressure is applied. Accordingly, the fact of requesting uniform dispersion of the ground pressure seems to be the reason compatible with the analysis of the small-sized tire.

Meanwhile, a large-sized tire having high rigidity/heavy load is provided with a totally inverse property in which in-plane slippage is extremely small even under an excessive vertical pressure and energy loss dissipated by the frictional energy is small. Small rolling resistance per load of a TB tire also supports the fact.

Further, even in the case of a TB tire, a block pattern of a rib-lug-type, above all, all weather type constituting a main current domestically shows a property similar to that of a small-sized tire in the use of a tractor head requiring a small turning radius and high traction performance.

In order to cover such a wide condition of use and property, there is needed a method of setting a region of a calculation object for differentiating an adhering region having small slippage from a slipping region causing slippage and taking out only wear energy contributing to wear of tread.

Hence, in view of the above-described problem, the invention provides a method capable of easily analyzing frictional energy of a rolling tire.

SUMMARY OF THE INVENTION

According to a first claim of the invention, there is provided a method of measuring a frictional energy M at inside of a contact patch at one point of a tread by rolling a tire, the method comprising the steps of:

(1) measuring step:
  at which an in-plane pressure Pxy(L) and a vertical pressure Pz(L) in respect of a contact length L from a front end of contact to a rear end of contact at the one point are measured; and
  a slip amount Sxy(L) in respect of the contact length L from the front end of contact to the rear end of contact at the one point is measured;
(2) restraining frictional force calculating step:
  at which a static frictional force based on Pxy(L) and Pz(L) measured at the measuring step is calculated as specified below
  Static frictional force $R(L)=|Pxy(L)|/|Pz(L)|$;
(3) maximum value calculating step:
  at which primary maximum values of R(L) calculated at the static frictional force calculating step are calculated to determine one of the primary maximum values disposed most proximately to the front end of contact as a maximum static frictional force Rm;
(4) contact length calculating step:
  at which a range of the contact length L in correspondence with R(L) having a value equal to or larger than Rm is determined as a slipping region LR when Rm is calculated in the maximum value calculating step;
(5) vertical pressure calculating step:
  at which Pz(LR) in correspondence with the slipping region LR calculated at the contact length calculating step is calculated from Pz(L) measured at the measuring step; and
(6) frictional energy calculating step:
  at which a sum E of a work amount which is a product of PZ(LR) calculated at the vertical pressure calculating step by Sxy(L) measured at the measuring step is calculated to determine a value of the sum E of the work amount multiplied by a proportional constant α as the wear energy M by determining that resilience energy stored in an adhering region is released in the slipping region.

According to the first claim of the method of analyzing frictional energy of a rolling tire, a range of LR having a value larger than the static frictional force constitutes the slipping region and the wear energy M is calculated such that friction is caused in the slipping region LR.

According to a second claim of the invention, there is provided a method of measuring a wear energy M at inside of a contact patch at one point of a tread by rolling a tire, said method comprising the steps of:
(1) measuring step:
  at which an in-plane pressure Pxy(L) and a vertical pressure Pz(L) in respect of a contact length L from a front end of contact to a rear end of contact at the one point are measured; and
  a slip amount Sxy(L) in respect of the contact length L from the front end of contact to the rear end of contact at the one point is measured;
(2) restraining frictional force calculating step:
  at which a static frictional force is calculated as specified below based on Pxy(L) and Pz(L) measured at the measuring step
  Static frictional force $R(L)=|Pxy(L)|/|Pz(L)|$
(3) maximum value calculating step:
  at which primary maximum values of R(L) calculated at the static frictional force calculating step is calculated; and (4) frictional energy calculating step:
  at which a sum E of a work amount which is a product of Pxy(L) by Sxy(L) from the front end of contact to the rear end of contact measured at the measuring step is calculated when the primary maximum values are not calculated at the maximum value calculating step to determine a value of the sum E of the work amount multiplied by a proportional constant a as the wear energy M.

According to the second claim of the method of analyzing frictional energy of a rolling tire, when the maximum static frictional force is not calculated, the frictional energy M is calculated such that a total of from the front end portion to the rear end portion of contact constitute the slipping region LR.

DETAILED DESCRIPTION OF THE PREFERRED EMBODIMENTS

First, before explaining a method of analyzing frictional energy of a rolling tire according to the invention, an explanation will be given of technical content of the invention.

Figure 1:
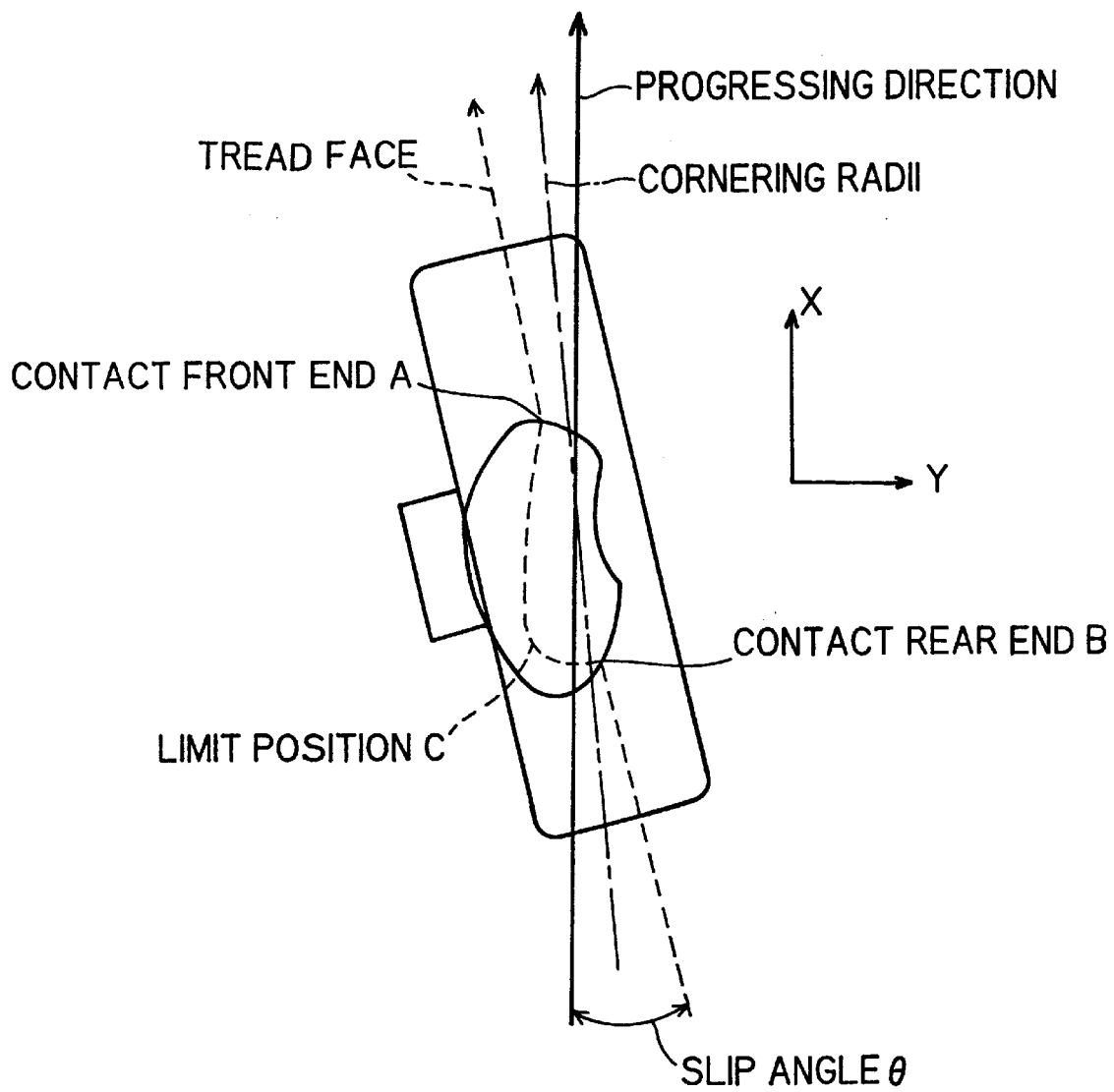
FIG. 1 is a plane view of a tire for explaining the theory of the invention.

FIG. 1 is a plane view of a basic phenomenon model of a generally used rolling tire and is a drawing in providing a slip angle θ.

In the drawing, as shown by an arrow mark of a dotted line of a tread face the tire is deformed in the minus direction of Y axis by frictional force of rubber starting from a front end portion of contact A of tire. While an amount of the deformation increases as the position proceeds thru the contact patch, resilience energy of elastic deformation is stored to a limit of the frictional force. The position is designated as a limit position C.

A portion of the frictional energy is released from the limit position C to a rear end portion of contact B and the frictional energy is dissipated in wearing the tire.

Accordingly, as shown by the drawing, a region from the front end portion of contact A to the limit position C can be determined as an adhering region, the frictional energy is not generated and is not dissipated in wearing the tire. Meanwhile, a region from the limit position C to the rear end portion of contact B can be determined as a slipping region and the frictional energy generated in the region seems to be dissipated in wearing the tire.

According to the invention, attention is paid to the adhering region and the slipping region and a range LR of contact length of only the slipping region is calculated and the wear energy M is calculated by pressure Pz in the vertical direction in correspondence with the slipping region LR.

Explaining further in details, the actual static frictional force varies depending on a measured position in the tread radial direction. This is because the vertical pressure Pz applied on a measured location is not necessarily uniform owing to a property which is characteristic to a TB tire in which the vertical pressure Pz applied on the measured point varies from a maximum value at the center portion to minimum values at both ends of tread and block stiffness variation from combination of tread rubber compound, radius of curvature of tread and so on or a rib pattern. Therefore, it is very difficult to specify the slipping region by determining slip limit frictional force at respective measured points from a static frictional coefficient of the road surface.

However, according to a rolling tire, sidewall deformation from tire load, a depression or flattening of tire tread radius occurs immediately before the tread portion enters the ground contact patch, causing large deformation and slippage referred to as wiping tread action at the front end portion of ground contact. Accordingly, regardless of tire category, the front end portion of contact is suitable for a measured position for calculating maximum static frictional force (resultant force of adhering frictional force and deformation loss frictional force).

At the front end portion of ground contact, although a slipping region is constituted by yielding to deformation pressure within the contact patch generated by large deformation coupled with low vertical pressure at the initial stage of ground contact, a movement caused by the absolutely small deformation pressure within the in-plane direction is restrained as the vertical pressure Pz increase as the tire rolls.

Accordingly, a value maximizing a ratio of absolute values of in-plane pressure Pxy and vertical pressure Pz at the front end portion of contact seems to be the maximum static frictional force of the measured point.

When a ratio exceeding the value of the maximum static frictional force is measured within the plane, it can be determined to constitute the slipping region as an object of integrating the frictional energy and when the ratio is equal to or smaller than the value, the adhering region other than the object of integration seems to be constituted.

The invention is embodied based on the above-described technical content.

First Embodiment

An explanation will be given as follows of a first embodiment of the invention in reference to FIG. 2 through FIG. 5 in view of the above-described technical content.

The first embodiment relates to an analyzing method concerning a TB tire.

Figure 2:
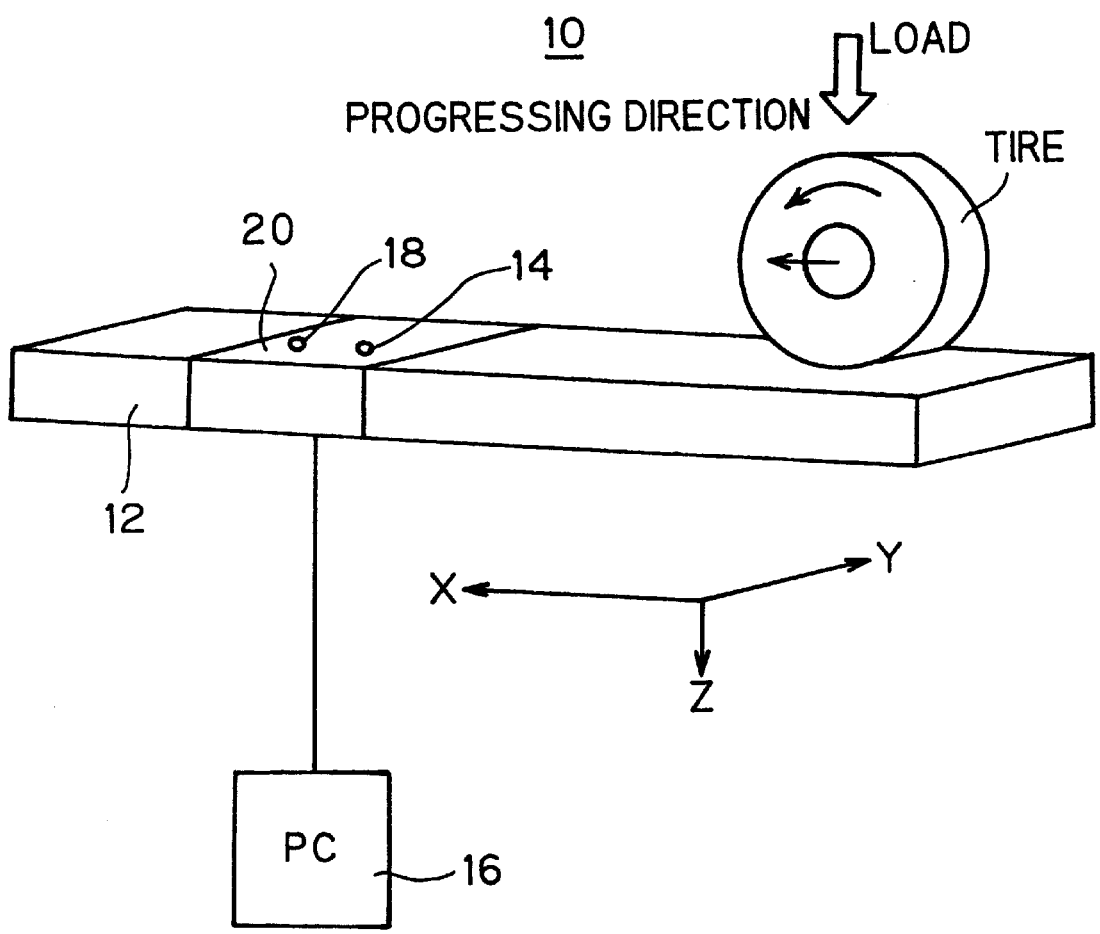
FIG. 2 is a block diagram showing a measuring apparatus of an embodiment.

FIG. 2 is a block diagram of a measuring apparatus 10 used in the analyzing method.

First, an explanation will be given of the measuring apparatus 10.

According to the measuring apparatus 10, a tire T constituting an object of measurement is rolled on a test bench 12 and in the movement, in-plane pressure Px(L) and Py(L) and vertical pressure Pz(L) are measured by using a pressure sensor 14 and slip amounts Sx(L) and Sy(L) are measured by using a deformation amount sensor 18. In this case, the tire T is applied with predetermined load.

Here, notation L designates a variable indicating a contact length and the contact position can be determined by the value of L. Further, specifically, a signal from the pressure sensor 14 is sampled at a predetermined frequency (for example, 500 Hz) and one of values of sampling is L. Therefore, for example, notation Pz(Lm) designates vertical pressure at a position of the contact length Lm representing a constant position.

The pressure sensor 14 detects pressure by strain gauges embedded in the test bench 12.

Further, according to the deformation amount sensor 18, a stylus is embedded into a road face 20 of the measuring apparatus 12 and when the tire passes through an upper portion thereof, the stylus pierces the surface of tread and movement of the surface of the grounding tread is detected by strain gauges.

Px(L), Py(L), Pz(L) detected by the pressure sensor 14 and Sx(L) and Sy(L) detected by the deformation amount sensor 18 are inputted to a personal computer (hereinafter, referred to as PC) 16 and there is carried out an analyzing processing explained below.

Further, the measuring apparatus 10 is used also in a second embodiment and a third embodiment, explained below.

An explanation will be given of a case of analyzing wear energy M by PC 16 with a TB tire as an object of measurement in the above-described measuring apparatus 10.

1. First step

There are measured by the measuring apparatus 10, a scalar amount Px(L) in X-axis direction of in-plane pressure as well as a scalar amount of Py(L) thereof and a scalar amount in Z-axis direction, that is, vertical pressure Pz(L) with regard to the contact length L from the front end portion of contact A to the rear end portion of contact B at one point in the TB tire.

Further, the in-plane pressure Pxy(L) is calculated from Px(L) and Py(L) by PC 16 in accordance with Equation (1).

$$Pxy(L)=\{Px(L)^2+Py(L)^2\}^{1/2} \quad (1)$$

Similarly, there are measured a scalar amount Sx(L) in X-axis direction and a scalar amount Sy(L) in Y-axis direction of a slip amount with regard to the contact length L from the front end portion of contact A to the rear end portion of contact B at one point of the TB tire.

Further, a slip amount Sxy(L) is calculated from Sx(L) and Sy(L) by PC 16 in accordance with Equation (2).

$$Sxy(L)=\{Sx(L)^2+Sy(L)^2\}^{1/2} \quad (2)$$

Further, all of the step and later steps are processed by PC 16.

2. Second step

Static frictional force R(L) is calculated based on Pxy(L) and Pz(L) measured at the first step.

R(L) is calculated in accordance with Equation (3).

$$R(L)=|Pxy(L)|/|Pz(L)| \quad (3)$$

Figure 3:
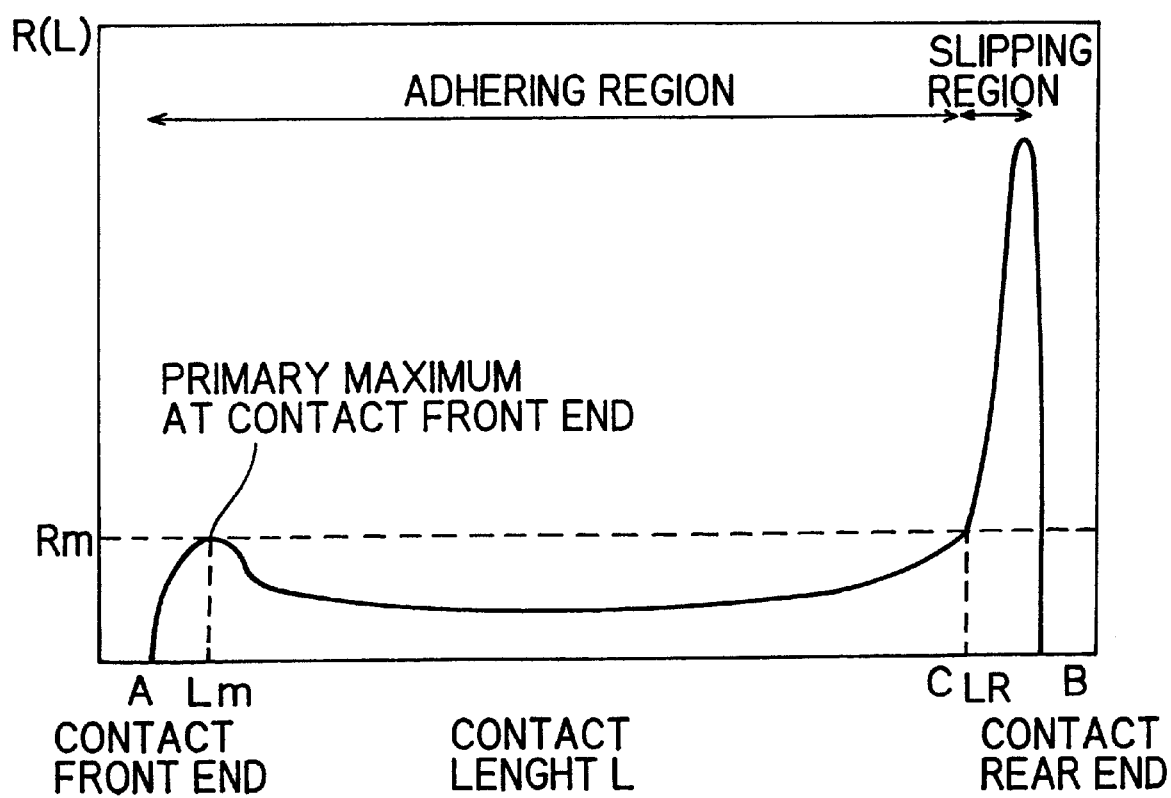
FIG. 3 is a graph showing a result of measurement according to a first embodiment.

In respect of Equation (3), a graph shown by FIG. 3 with the abscissa of L and the ordinate of R(L) is outputted to an attached printer or a display. Further, when the contact length L from the front end portion of contact A to the rear end portion of contact B is converted into a time period in the graph, the time is about 0.1 second to about 1 second and the graph can be displayed also time-sequentially.

3. Third step

As shown by the graph of FIG. 3, a primary maximum value Rm of R(L) calculated in the second step is calculated. Further, Rm is provided with a value most proximate to the front end portion of contact A in primary maximum values.

That is, as mentioned above, according to a rolling tire, sidewall deformation from tire load, a depression or flattening of the tire tread radius occurs immediately before the tread portion enters the ground contact patch, causing slippage referred to as wiping tread action by large deformation and accordingly, the front end portion of contact is suitable for calculating the maximum static frictional force regardless of category of tire. Further, the primary maximum value Rm is the maximum static frictional force.

4. Fourth step

When the primary maximum value Rm is calculated at the third step, a range of the contact length L with regard to R(L) having a value equal to or larger than Rm is determined as a slipping region LR. That is, it is determined as shown by FIG. 3 that the initially emerged primary maximum value Rm indicates the maximum frictional force and therefore, a contact position at which the maximum static frictional force Rm is exceeded successively indicates the limit position C in FIG. 1 and a contact range LR reaching the rear end portion of contact B thereafter constitutes a slipping region which is a portion where the frictional energy is generated. Further, the "slipping region LR" can be defined as a set of points of contact positions where the maximum static frictional force Rm is exceeded and is not a dimension representing a length.

5. Fifth step

PZ(LR) in respect of the slipping region LR calculated at the fourth step is calculated from Pz(L) measured at the second step.

6. Sixth step

A sum of the product (work amount) of PZ(LR) calculated at the fifth step multiplied by Sxy(L) is calculated by Equation (4). That is, integration is carried out over an entire face in the slipping region LR in the slipping region and a sum E of the work amount is calculated.

$$E = \int_{LR} P_Z(L) \cdot S_{xy}(L) dL \quad (4)$$

Further, by multiplying the calculated sum E of work amount by a predetermined proportional constant a, the wear energy M can be calculated.

$$M = \alpha \cdot E \quad (5)$$

In this way, the wear energy M at one point in the tread portion of the TB tire can be calculated.

Figure 4:
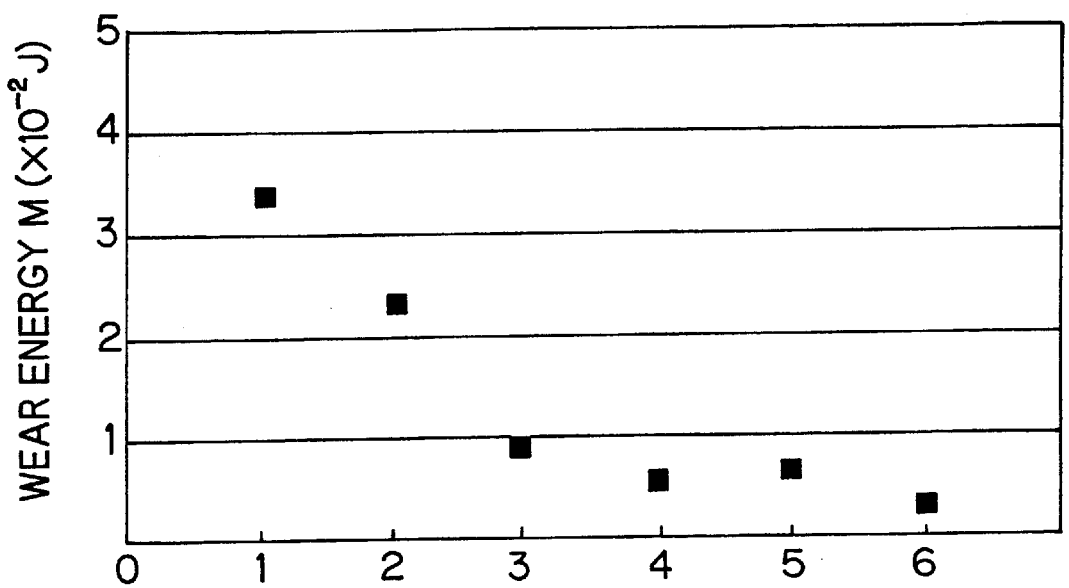
FIG. 4 is a graph showing a relationship of wear energy provided by the measurement result.

The wear energy is calculated by the above-described analyzing method at respective points in the width direction of the tread of the TB tire and graphed as shown by FIG. 4. The ordinate designates the wear energy M and the abscissa designates measured points (in this case, measured at six points and a side of 0-th measured point indicates an outer side of the tire).

Figure 5:
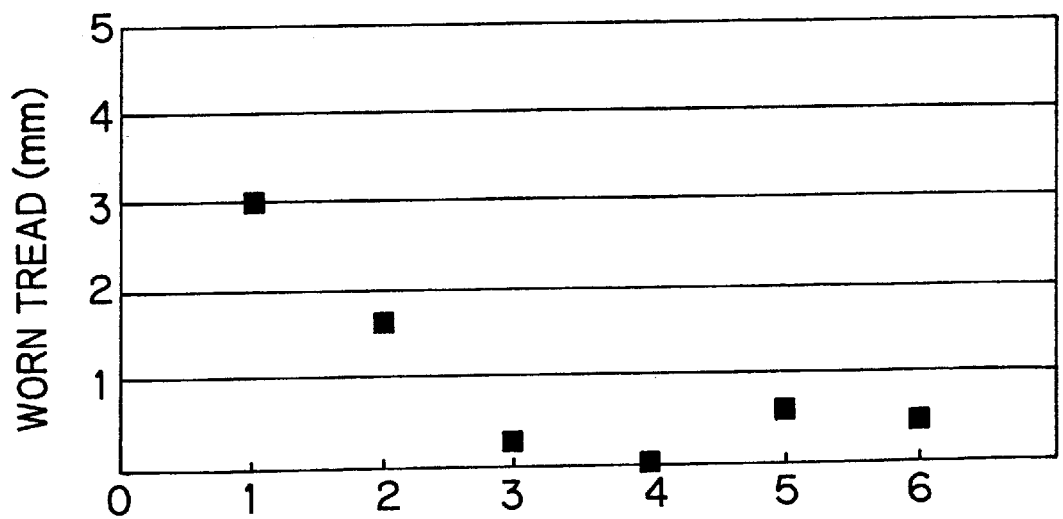
FIG. 5 is a graph showing a relationship of a worn tread provided by an actual test.

Further, FIG. 5 shows a worn state in the case of running 8,800 km, the ordinate designates a wear amount and the abscissa designates the same measured points.

When FIG. 4 is compared with FIG. 5, there is a tendency in which the larger the wear energy M, the larger the wear amount, which indicates accuracy of the analyzing method.

Second Embodiment

According to the second embodiment, in place of the TB tire in the first embodiment, a tire for a passenger vehicle (hereinafter, referred to as PC tire) constitutes an object of measurement and is measured by using the measuring apparatus 10.

Figure 6:
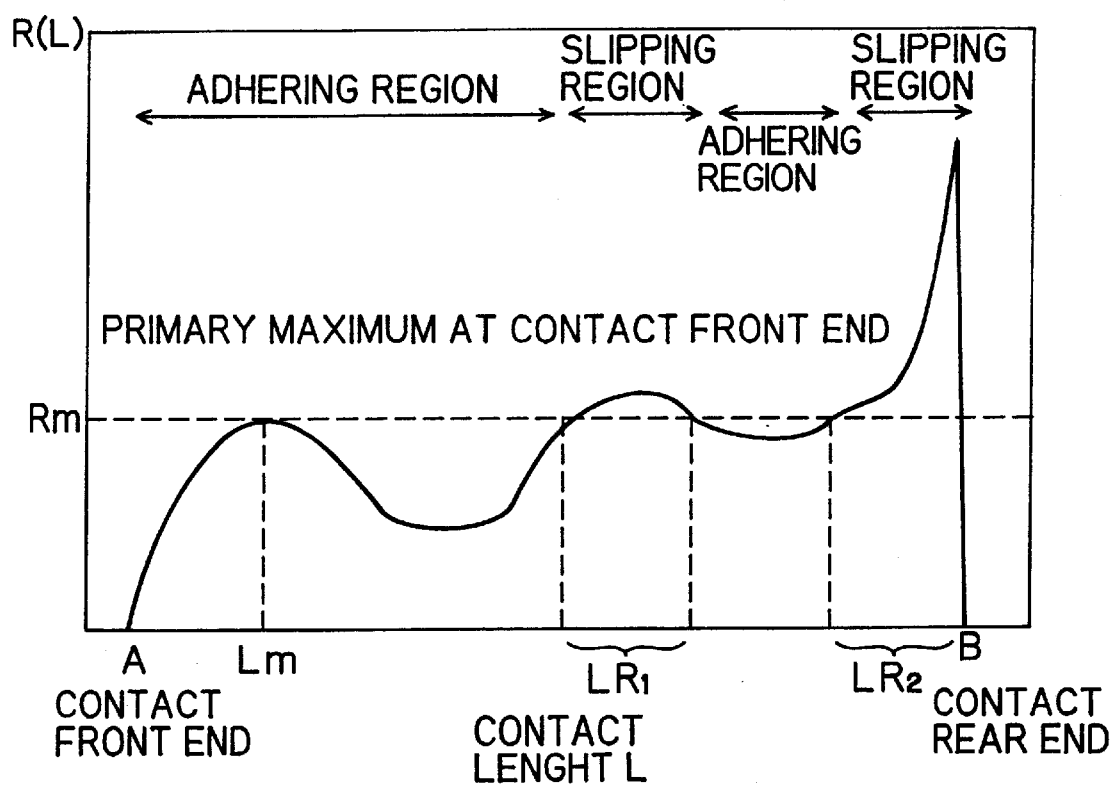
FIG. 6 is a graph showing a measurement result according to a second embodiment.

Similar to the first embodiment, the embodiment is graphed as shown by FIG. 6 also with R(L) on the ordinate and the contact length L on the abscissa.

Also in this case, the maximum static frictional force Rm is calculated and slipping regions LR1 and LR2 which are positions of the static frictional force having a value equal to or larger than Rm are calculated. Further, the frictional energy M is constituted by calculating a combination sum E of in-plane pressure Pxy(LR1) and vertical Pz(LR2) at the portions and multiplying the sum E by the proportional constant $\alpha$.

Combination of in-plane pressure for slippage within the contact length L and vertical pressure for slippage at the after end of contact is used because regional slip within the contact length L is restrained to a minimum by the surrounding tread.

In this case, as shown by FIG. 6, although the slipping region is produced in the TB tire at and after the limit position C, in the case of PC tire, the tendency differs therefrom slightly and there emerge the slipping regions at two locations. That is, the slipping regions are regions of LR1 and LR2 and two of the regions designate the slipping regions.

Accordingly, slip amounts Sxy(LR1) and Sxy(LR2) are measured in respect of the two regions and the sum E of the work amount is calculated from Equation (6) and the frictional energy M is calculated based on Equation (5).

$$E = \int_{LR1} P_{xy}(L) \cdot S_{xy}(L) dL + \int_{LR2} P_Z(L) \cdot S_{xy}(L) dL \quad (6)$$

The frictional energy M calculated in this way is proximate to the actual wear energy M.

Third Embodiment

Figure 7:
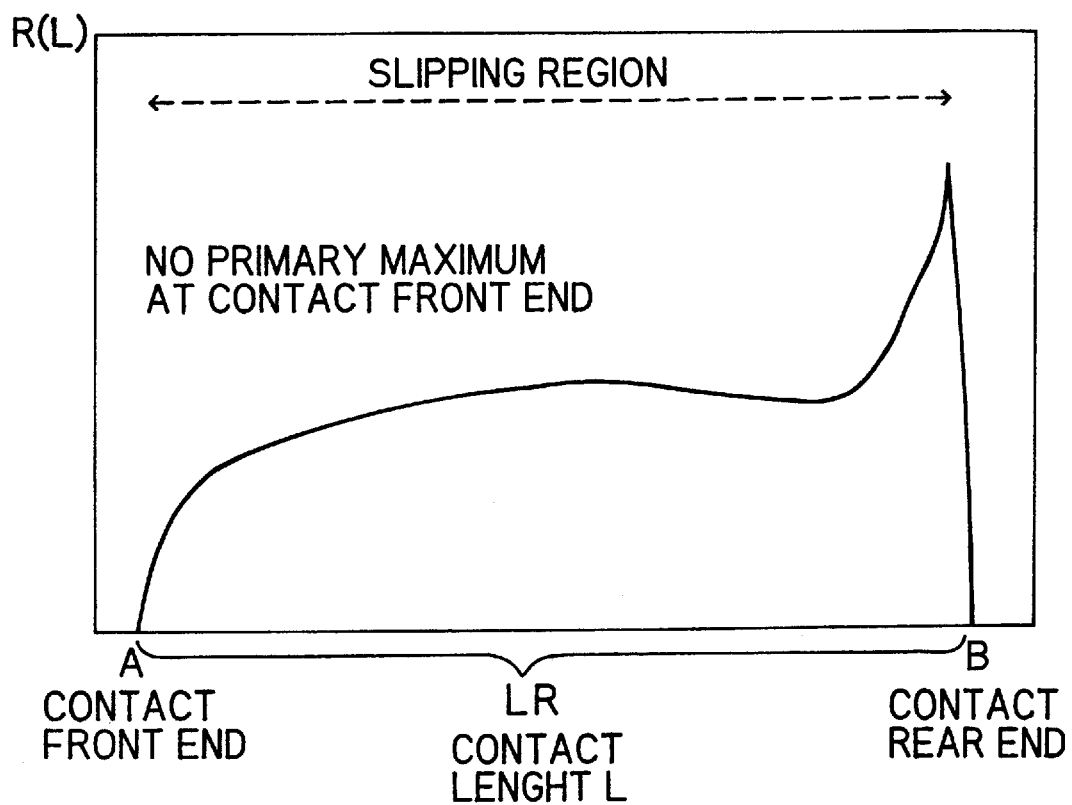
FIG. 7 is a graph showing a measurement result according to a third embodiment.

In the TB tire, there is a case in which the slipping region is produced on the entire face from the front end portion of contact A to the rear end portion of contact B. In this case, different from the first embodiment, the maximum static frictional force Rm, that is, the primary maximum value is not generated. FIG. 7 shows such a state.

When the primary maximum value cannot be calculated as mentioned above, it is determined that the slipping region is produced in the entire region, the contact length L from the front end portion of contact A to the rear end portion of contact B is determined as the slipping region LR and the frictional energy M is calculated.

According to the calculation method, the sum E of the work amount is calculated from Equation (7) by measuring Pxy(LR) and the slip amount Sxy(L) in correspondence with LR and the frictional energy M is calculated therefrom based on Equation (5).

$$E = \int_L P_{xy}(L) \cdot S_{xy}(L) dL \quad (7)$$

The frictional energy M calculated in this way is proximate to the actual wear energy M.

As described above, according to the embodiment, even when the primary maximum value is not calculated, by making the entire region to be the slipping region, the frictional energy can be measured accurately.

INDUSTRIAL AVAILABILITY

As mentioned above, according to the method of analyzing frictional energy of a rolling tire of the invention, a portion where the static frictional force is equal to or larger than the maximum static frictional force Rm is determined as the slipping region LR and the wear state can accurately be grasped by paying attention to the fact that the frictional energy is produced at the slipping region LR.

Further, when the maximum static frictional force Rm is not calculated, by determining the entire region as the slipping region LR, the wear state can be grasped accurately also in this case.

What is claimed is:

1. A method of measuring a frictional energy M or wear at inside of a contact patch at one point of a tread by rolling a tire, said method comprising the steps of:

(1) measuring step:
 at which an in-plane pressure Pxy(L) and a vertical pressure Pz(L) in respect of a contact length L from a front end of contact to a rear end of contact at the one point are measured; and
 a slip amount Sxy(L) in respect of the contact length L from the front end of contact to the rear end of contact at the one point is measured;

(2) static frictional force calculating step:
 at which a static frictional force is calculated as specified below based on Pxy(L) and Pz(L) measured at the measuring step Static frictional force R(L)=|Pxy(L)|/|Pz(L)|

(3) maximum value calculating step:
 at which primary maximum values of R(L) calculated at the static frictional force calculating step are calculated to determine one of the primary maximum values disposed most proximately to the front end of contact as a maximum static frictional force Rm;

(4) contact length calculating step:
 at which a range of the contact length L in correspondence with R(L) having a value equal to or larger than Rm is determined as a slipping region LR when Rm is calculated in the maximum value calculating step;

(5) vertical pressure calculating step:
 at which Pz(LR) in correspondence with the slipping region LR calculated at the contact length calculating step is calculated from Pz(L) measured at the measuring step; and (6) frictional energy calculating step:
 at which a sum E of a work amount which is a product of Pz(LR) calculated at the vertical pressure calculating step by Sxy(L) measured at the measuring step is calculated to determine a value of the sum E of the work amount multiplied by a proportional constant $\alpha$ as the wear energy M.

2. A method of measuring a frictional energy M or wear at inside of a contact patch at one point of a tread by rolling a tire, said method comprising the steps of:

(1) measuring step:
 at which an in-face pressure Pxy(L) and a vertical pressure Pz(L) in respect of a contact length L from a front end of contact to a rear end of contact at the one point are measured; and
 a slip amount Sxy(L) in respect of the contact length L from the front end of contact to the rear end of contact at the one point is measured;

(2) static frictional force calculating step:
 at which a static frictional force is calculated as specified below based on Pxy(L) and Pz(L) measured at the measuring step Static frictional force R(L)=|Pxy(L)|/|Pz(L)|;

(3) maximum value calculating step:
 at which primary maximum values of R(L) calculated at the static frictional force calculating step are calculated; and (4) frictional energy calculating step:
 at which a sum E of a work amount which is a product of Pxy(L) by Sxy(L) from the front end of contact to the rear end of contact measured at the measuring step is calculated when the primary maximum values are not calculated at the maximum value calculating step and a value of the sum E of the work amount multiplied by a proportional constant $\alpha$ is determined as the wear energy M.

* * * * *